(12) United States Patent
Terwilliger

(10) Patent No.: US 7,167,808 B2
(45) Date of Patent: Jan. 23, 2007

(54) STATISTICAL DENSITY MODIFICATION USING LOCAL PATTERN MATCHING

(75) Inventor: Thomas C. Terwilliger, Santa Fe, NM (US)

(73) Assignee: Los Alamos National Security, LLC, Los Alamos (MX)

( * ) Notice: Subject to any disclaimer, the term of this patent is extended or adjusted under 35 U.S.C. 154(b) by 356 days.

(21) Appl. No.: 10/821,235

(22) Filed: Apr. 8, 2004

(65) Prior Publication Data
US 2005/0228615 A1   Oct. 13, 2005

(51) Int. Cl.
G06F 15/00 (2006.01)
G01N 31/00 (2006.01)

(52) U.S. Cl. .................. 702/180; 702/27; 702/179
(58) Field of Classification Search .......... 702/22, 702/23, 27, 179, 180, 181
See application file for complete search history.

(56) References Cited
U.S. PATENT DOCUMENTS
2003/0046011 A1 * 3/2003 Friedman ............... 702/27

\* cited by examiner

Primary Examiner—John Barlow
Assistant Examiner—Meagan S Walling
(74) Attorney, Agent, or Firm—Bruce H. Cottrell; Ray G. Wilson

(57) ABSTRACT

A computer implemented method modifies an experimental electron density map. A set of selected known experimental and model electron density maps is provided and standard templates of electron density are created from the selected experimental and model electron density maps by clustering and averaging values of electron density in a spherical region about each point in a grid that defines each selected known experimental and model electron density maps. Histograms are also created from the selected experimental and model electron density maps that relate the value of electron density at the center of each of the spherical regions to a correlation coefficient of a density surrounding each corresponding grid point in each one of the standard templates. The standard templates and the histograms are applied to grid points on the experimental electron density map to form new estimates of electron density at each grid point in the experimental electron density map.

7 Claims, 15 Drawing Sheets

Identify the probability distribution $p$ at $x$ in high quality maps as a function of the two templates that best match the local modified density at $x$      90

At each point $x$ in a high quality map, identify the two templates $k$, $l$ that have the highest and next-highest correlation coefficients, respectively, with the local modified density at $x$      92

Construct histograms by tabulating the value of the (unmodified) electron density $p(x)$ as a function of $k$ and $l$      94

Normalize histograms to yield an estimate of the probability distribution, $p(p\backslash k,l)$      96

*FIG. 5*

Compute the probabilities $p(cc_k|cc_{obs,k})$ that the correlation coefficient for template $k$ to a point $x$ in a high quality map would have the value $cc_k$, given the observation that this template has a correlation coefficient $cc_{obs,k}$ to the same point in a map with additional errors  100

Create paired sets of high-quality experimental maps with and without added errors  102

At each point in a map, identify the correlation coefficient of each template $k$ to the maps without added errors, $cc_k$, and the correlation with added errors, $cc_{obs,k}$  104

Create a histogram of the correlation $cc_k$ as a function of the correlation $cc_{obs,k}$. Normalize the resulting histograms to yield the probability $p(cc_k|cc_{obs,k})$ that $cc_k$ is the correlation to the map without added errors if the value $cc_{obs,k}$ is observed in the map with added errors  106

Repeat for maps with varying levels of additional errors by creating simulated phase sets with Gaussian distributions of phase errors with varying overall values of the cosine of the phase error $\langle cos\Delta\phi \rangle$, ranging typically from 0.5 to 0.8  108

*FIG. 6*

FIG. 9A        FIG. 9B
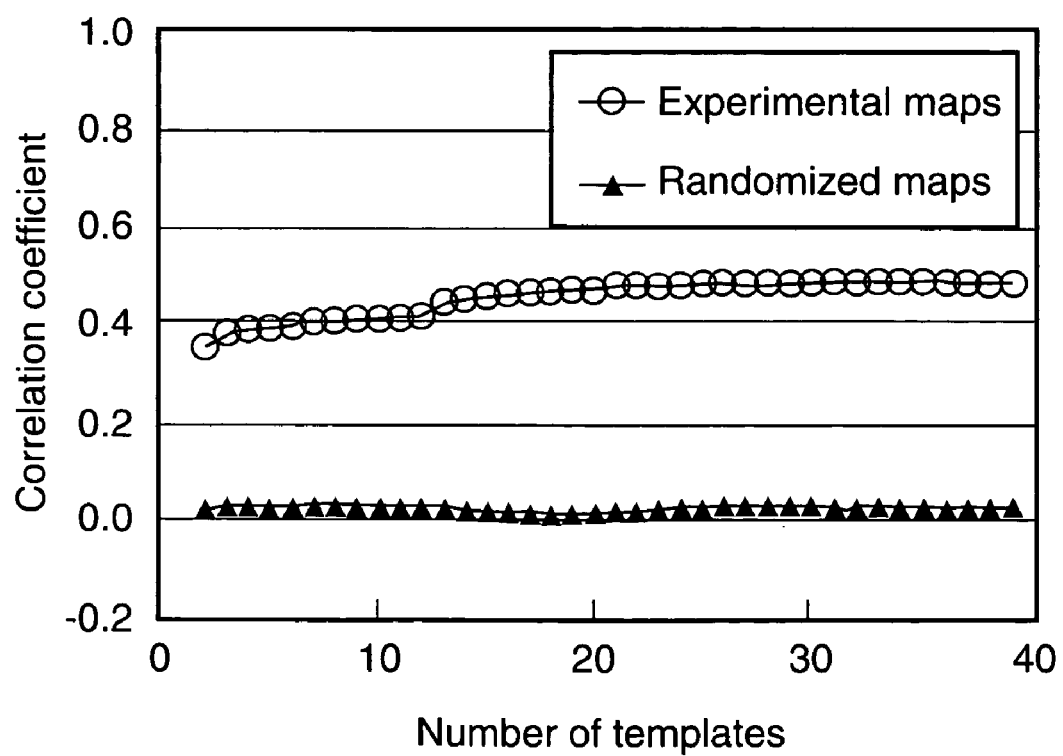
FIG. 10

STATISTICAL DENSITY MODIFICATION USING LOCAL PATTERN MATCHING

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to electron density maps of protein structures, and, more particularly, to the use of local patterns of electron density to improve estimates of electron density at each point in experimental electron density maps.

COMPUTER PROGRAM COMPACT DISK APPENDIX

One embodiment of the present invention is contained in the computer program compact disk, two copies of which are attached. The contents of the compact disk are incorporated by reference herein for all purposes.

| File Name | Date Created | File Size |
|---|---|---|
| resolve_pattern_2.05.f | Jul. 7, 2003 | 1,028 KB |
| resolve_2.05.f | Jul. 7, 2003 | 5,935 KB |
| resolve_pattern_allocate_2.05.c | Jul. 7, 2003 | 38 KB |
| resolve_allocate-2.05.c | Jul. 7, 2003 | 43 KB |
| tabulate.f | Jul. 7, 2003 | 82 KB |
| index_setup.f | Jul. 7, 2003 | 59 KB |
| analyze_tabulate.f | Jul. 7, 2003 | 71 KB |

The contents of the compact disks are subject to copyright protection. The copyright owner has no objection to the reproduction of the contents of the compact disk from the records of the U.S. Patent and Trademark Office, but otherwise reserves all copyright rights whatsoever.

BACKGROUND OF THE INVENTION

Electron density maps corresponding to macromolecules such as proteins have features that are different in fundamental ways from features found in maps calculated with random phases. These differences have been used in many ways, ranging from improving the accuracy of crystallographic phases to evaluating the quality of electron density maps ("maps" herein). For example, maps corresponding to proteins often have large regions of relatively featureless solvent, and large regions containing polypeptide chains, while a map calculated with random phases has similar fluctuations in density everywhere (Bricogne, 1974). This observation is the basis of the powerful solvent flattening approach (Bricogne, 1974; Wang, 1985) as well as methods for evaluating the quality of macromolecular electron density maps (e.g., Terwilliger et al., 1999). Similarly, the presence of non-crystallographic symmetry in macromolecular electron density maps has been useful in phase improvement (Bricogne, 1974, Rossmann, 1972; Kleywegt et al., 1998). Additionally, maps corresponding to macromolecules can be interpreted in terms of atomic models, providing a powerful basis for map quality evaluation and improvement (Agarwal et al., 1977; Lunin et al., 1984; Lamzin et al., 1993; Perrakis et al, 1997, 1999, 2001; Morris et al., 2002). On a statistical level, the density in the protein region of a macromolecular electron density map has a distribution that is very different than that in a map calculated with random phases. This has been extensively used in histogram-matching and related methods for phase improvement (Harrison, 1988; Lunin, 1988; Zhang et al., 1990; Zhang et al., 1997; Goldstein et al., 1998; Nieh et al., 1999; Cowtan, 1999).

The process of the present invention considers local patterns of density that are common in macromolecular protein structures. Macromolecules are built from small, regular, repeated units, and the packing of these units is highly constrained due to van der Waals interactions. Due to the regularity of macromolecules on a local scale, their electron density maps have local features that are distinctive and very different from those of maps calculated from random phases (Lunin, 2000; Urzhumtsev et al., 2000; Main et al., 2000; Wilson et al., 2000; Colovos et al., 2000). This property has been used to evaluate the quality of electron density maps and to improve phases at low resolution. For example, Lunin, 2000, Urzhumtsev et al., 2000, Main et al., 2000, and Wilson et al., 2000, use histogram and wavelet analysis to improve electron density in low-resolution maps by requiring the wavelet coefficients to be similar to those of model structures. Colovos et al., 2000, analyze the local features of high- and medium-resolution electron density maps and compare those features to corresponding features in model maps to evaluate the quality of the maps and suggest that their approaches may be useful for phase improvement as well.

A recent method for density modification consists of the identification of the locations of helical or other highly regular features in an electron density map, followed by statistical density modification using an idealized version of this density as the "expected" electron density nearby (Terwilliger, 2001). This method was shown to yield some phase improvement, but has the disadvantage that, after an initial cycle, the features that were initially identified became greatly accentuated, and few new features could be found. This effect may arise from the inherent feedback in the method, where a feature in the original electron density that partially matches a helical template is restrained to look like this template, making it an even better match for the template on the next round (even if the true density in the region is not helical).

The present invention uses the information inherent in local features of an electron density map that does not have this feedback to provide a capability for improvement in the features of the resulting electron density map, with concomitant improvement in the experimental phase information. The local patterns of density surrounding any point in a map have been found to be useful to estimate the electron density at that point. This observation makes it possible to begin with an electron density map with errors, to obtain a new estimate of the density at each point in the map without using the density at that point, and thereby to construct a new estimate of electron density with errors that are nearly uncorrelated with the errors in the original map. This recovered "image" of the electron density has many uses, including phase improvement and evaluation of map quality.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes a computer implemented method for modifying an experimental electron density map. A set of selected known experimental and model electron density maps is provided and standard templates of electron density are created from the selected experimental and model electron density maps by clustering and averaging values of electron density in a spherical region about each point in a grid that defines each selected known experimental and model electron density maps. Histograms are also created from the selected experimental and model electron density maps that relate the value of electron density at the center of each of the spherical regions to a correlation coefficient of a density surrounding each corresponding grid point in each one of the standard templates. The standard templates and the histograms are applied to grid points on the experimental electron density map to form new estimates of electron density at each grid point in the experimental electron density map.

In one embodiment, the process excludes electron density information from each grid point as clustering and averaging values are generated for that grid point and as histograms are generated for that grid point.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings:

FIG. 5 is a flow diagram for examining the statistics of high quality known electron density maps.

FIG. 6 is a flow diagram for computing the probabilities that the correlation coefficient for a template k to a point x in a high quality map has a value $cc_k$.

FIGS. 9A and 9B graphically depict an original electron density map and an electron density map in which the density is adjusted to remove information about the density at a location x from the density in a volume about x.

FIG. 10 graphically illustrates that the correlations between patterns and densities at points in a map is a feature of protein-like maps and not a feature of maps with random phases.

DETAILED DESCRIPTION

Figure 1:
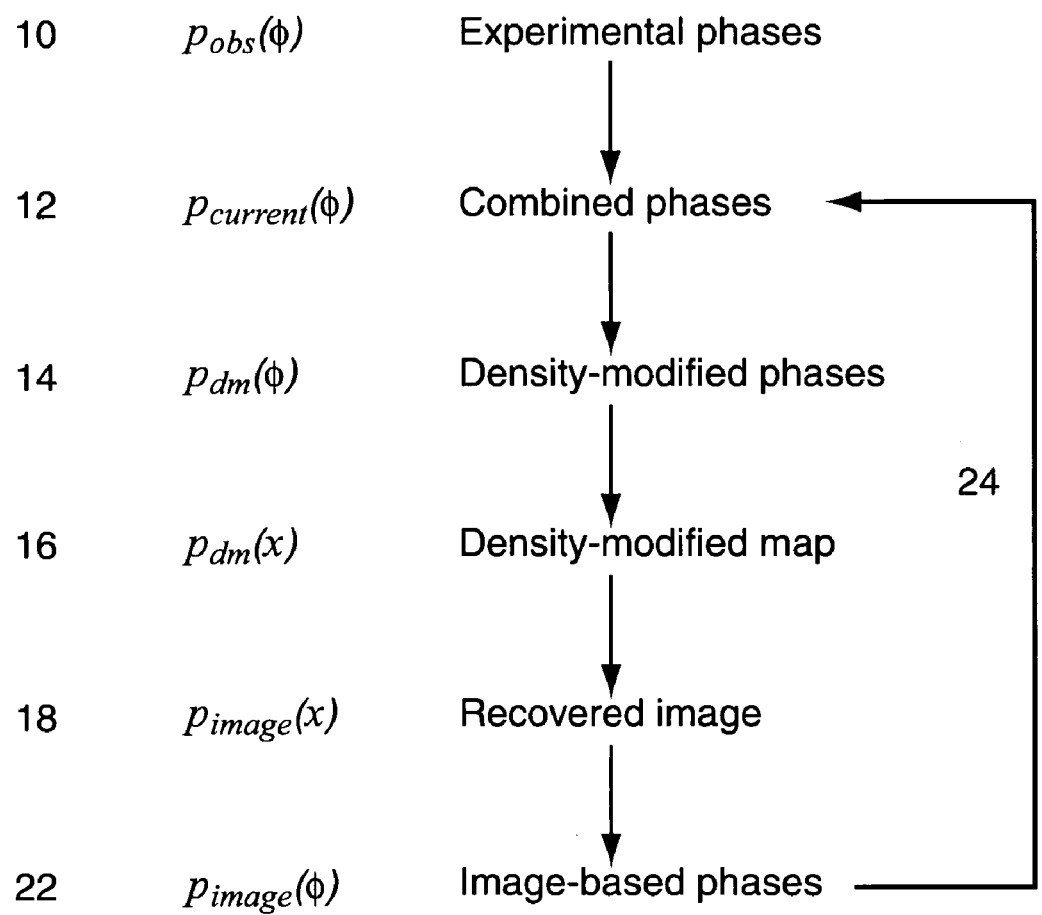
FIG. 1 is a flow diagram overview of the iterative process that combines the local pattern matching approach of the present invention with the statistical density modification procedures.

A computer implemented method for modifying an experimental electron density map is presented that is based on the preferential occurrence of certain local patterns of electron density in macromolecular electron density maps. The method focuses on the relationship between the value of electron density at a point in the map, and the pattern of density in a spherical region surrounding this point. Patterns of density that can be superimposed by rotation about the center of this sphere are considered equivalent. It is preferred, without limitation, that the process of the present invention be performed using a programmed general purpose computer.

Standard templates of electron density are created from known experimental or model electron density maps by clustering and averaging local patterns of electron density. A pattern of electron density is a list of the values of electron density that are calculated on a grid in 3-dimensional space, as is well-known in the field of X-ray crystallography. The local region over which the density is calculated is a spherical region with a radius typically of about 2 Angstroms. The clustering is based on correlation coefficients that relate two patterns of electron density after rotation to maximize the correlation, where the correlation coefficient conventionally represents the tendency of two random variables X and Y to vary together, as given by the ratio of the covariance of X and Y to the square root of the product of the variance of X and the variance of Y.

Known experimental or model maps are also used to create histograms that relate the value of electron density at the center of the sphere to the correlation coefficient of the density surrounding this point with each member of the set of standard patterns. These histograms are then used to estimate the electron density at each point in a new experimental electron density map using the pattern of electron density at points surrounding the center of the sphere and the correlation coefficient of this density to each of the set of standard templates, again after rotation to maximize the correlation.

The method is strengthened by excluding any information from the point in question from both the templates and the local pattern of density in the calculation. A function based on the region near the origin of the Patterson function (Blundell and Johnson, 1976), which corresponds to the average correlation of density at one point with the density at neighboring points, is used to remove information about the electron density at the point in question from nearby electron density. This allows an estimation of the electron density at each point in a map using only information from other points in the process.

The Patterson function P(u) is a special three-dimensional function that can be calculated using the amplitudes of the structure factors for a crystal, without knowledge of the crystallographic phases. All electron density maps based on the same set of amplitudes (but any phases) have the same Patterson function. The Patterson function is the autocorrelation of the density $\rho(x)$ in the electron density map, given by the relation, $P(u)=\int_v \rho(x)\rho(x+u)dV$, where the integral is over the entire unit cell of the crystal. The origin of the Patterson function is the place at which u=(0,0,0). The value of the Patterson function at the origin is the integral over the entire unit cell of the square of the electron density.

The resulting estimates of electron density are shown to have errors that are nearly independent of the errors in the original map, using model data and templates calculated at a resolution of 2.6 Å. Due to this independence of errors, information from the new map can be combined by multiplying phase probabilities (Blundell & Johnson, 1976) with information from the original map to create an improved map.

The iterative phase-improvement process combines the local pattern matching approach of the present invention with statistical density modification procedures (e.g., U.S. patent applications Ser. No. 09/512,962, filed Feb. 25, 2000; Ser. No. 09/769,612, filed Jan. 23, 2001; and Ser. No. 10/017,643, filed Dec. 12, 2001, all incorporated herein by reference). This combined iterative approach has been applied to experimental data at resolutions ranging from 2.4 Å to 2.8 Å.

An overview of the iterative procedure that is used to combine the information from the recovered image with the information present in a new experimental electron density is shown in FIG. 1. In the first cycle, the starting phase probabilities are new experimental values 10, and, in all cycles, the amplitudes are the new experimental values. In each cycle, the starting phases and amplitudes are subjected to density modification 14 (e.g., statistical density modification using RESOLVE (file resolve_2.05c) or other related methods) to obtain the best possible electron density map without using any pattern-based information. Then this density-modified map is analyzed 16 for local patterns and an image of the map is recovered 18. Third, the density in the recovered image is used all by itself to estimate 22 phase probabilities. This third step is carried out here using statistical density modification (Terwilliger, 2000) as described below, but could be done using $\sigma_A$-based methods (Read, 1986). Finally, the phase probabilities from the recovered image are combined 12 with the original experimental phase probabilities to yield the starting phase probabilities for the next cycle. The process is iterated 24 until changes in the density-modified map from cycle to cycle are small (typically 1 to 5 cycles). The density-modified map from the final cycle is then suitable for interpretation.

Figure 2:
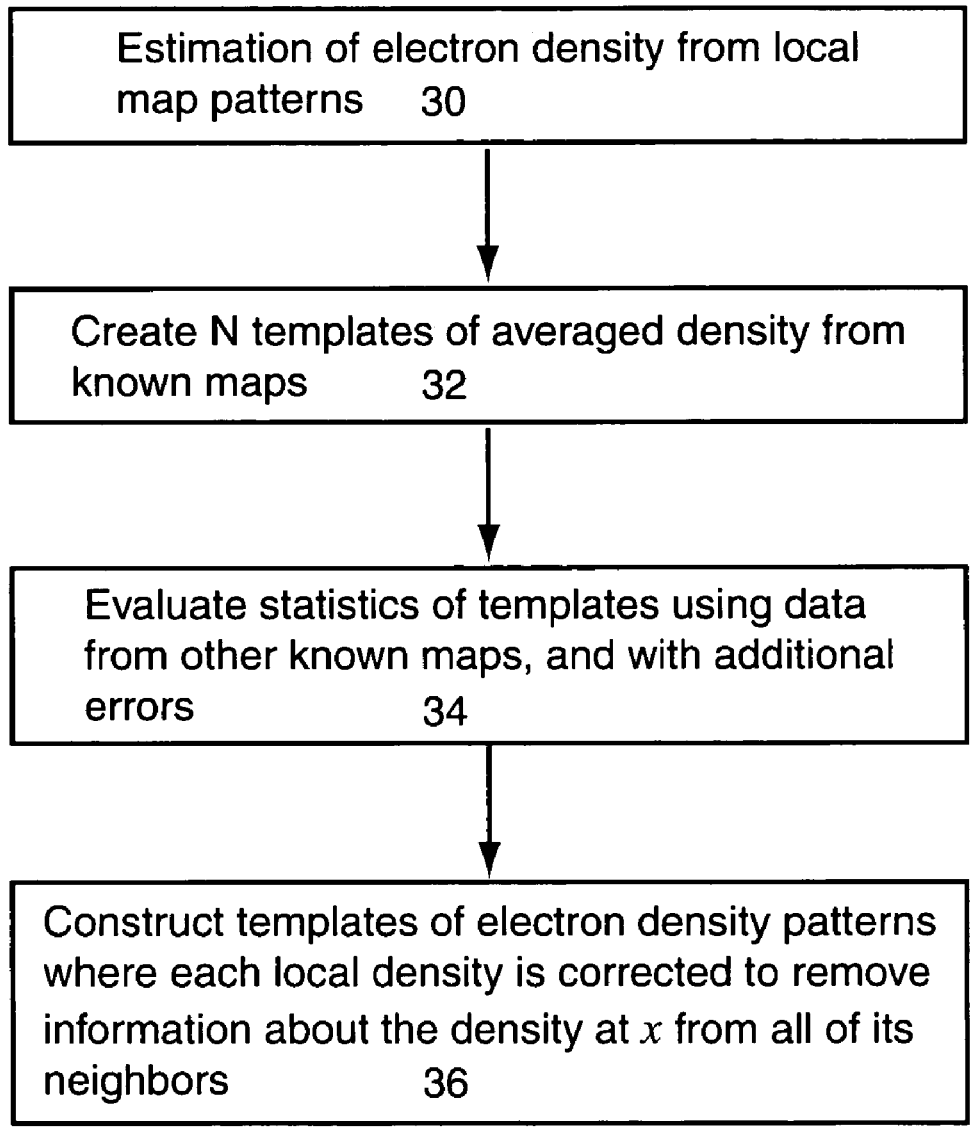
FIG. 2 is a flow diagram for estimating electron density from local patterns in an electron density map.

Estimation of Electron Density from Local Patterns in a Map (FIG. 2, Step 30)

In accordance with the process of the present invention, the density surrounding each point in a map is used to construct a new estimate of electron density at that point. There are three overall steps. The first two steps create templates 32 and evaluate statistics 34 of these templates using data from known experimental or model maps, with and without additional errors. The third step applies these results to new experimental maps. In exemplary applications described here, density-modified experimental maps obtained from Single or Multiple-wavelength Anomalous Diffraction (SAD/MAD) data at a resolution of 2.6 Å were used to create the templates and histograms, but a similar procedure could be carried out using either experimental or model maps at any resolution.

In the first step, N templates of averaged density are created. These templates are based on the local density in a known experimental or model protein electron density map that has been calculated using crystallographic phases that have been modified by "density modification," as carried out by, e.g., RESOLVE (File resolve_2.05.f, resolve_allocate_2.05.c, tabulate.f, analyze_tabulate.f, and index_setup.f), U.S. patent application Ser. No. 09/769,612, and are grouped by correlation coefficient. Second, the relationship between the density at point x and the template that has the highest correlation with the density surrounding x is tabulated using additional density-modified experimental electron density maps. Finally, the method is applied to other known experimental maps until the N templates have been created. The density near each point x in a map is used to construct 36 a new estimate of the density at x. In this process, the local density is corrected in a way that removes the information about the density at x from all its neighbors.

Figure 3:
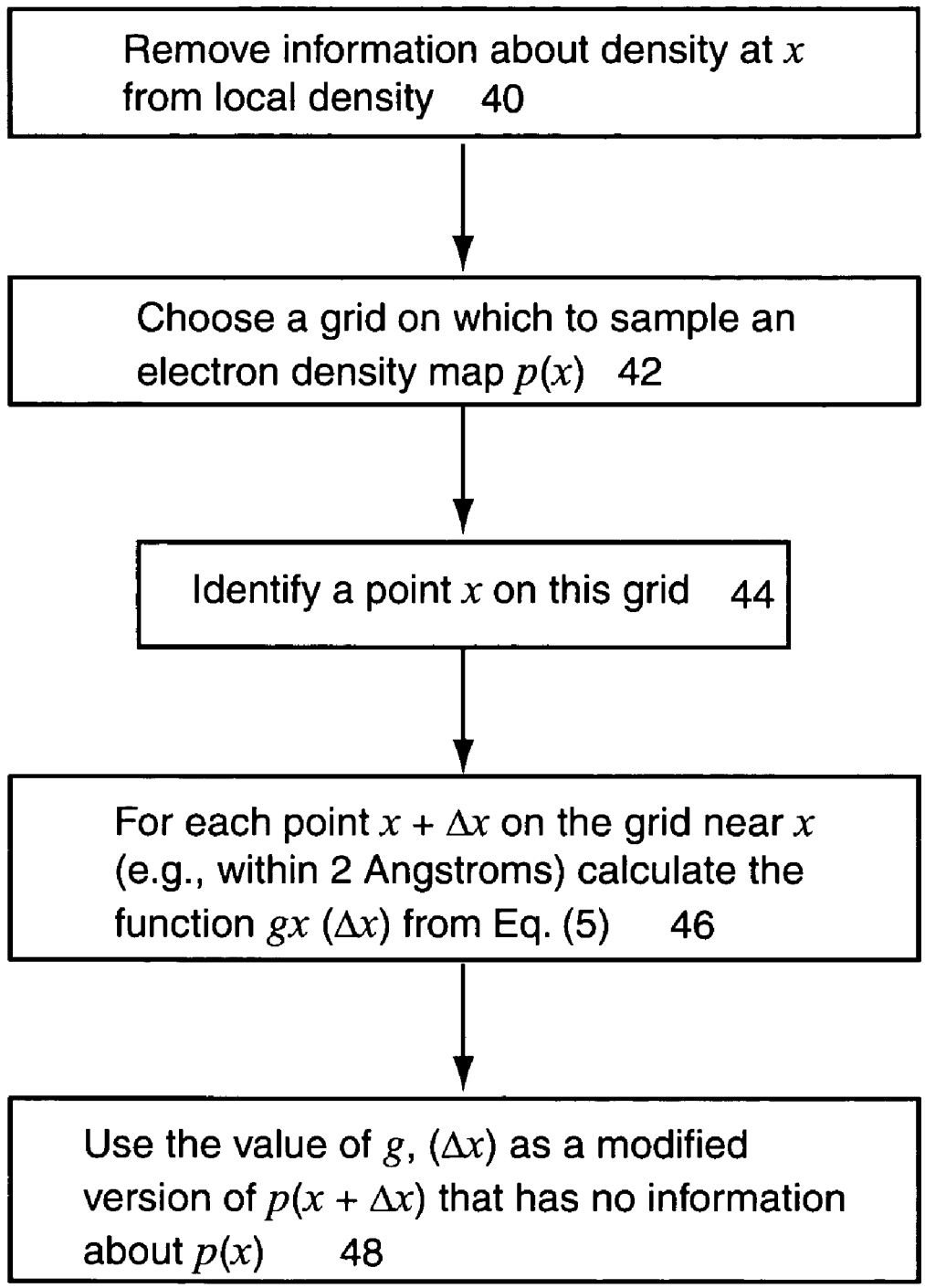
FIG. 3 is a flow diagram for a method to remove information about density at a specific point from density values computed in a volume about the location.

Removal of Information About Density at x from Local Density (FIG. 3, Step 40)

(File resolve_pattern_2.05.f: subroutines get_patt_norm (obtain values of the Patterson function near the origin), get_local_density (obtain density surrounding x, after removal of information about density at x using Eqs. (5), (6), and (7)))

A grid is selected 42 for sampling an electron density map, as is well known in the crystallography art. An estimate of the value of electron density at a grid point x 44 in the unit cell is obtained such that the new estimate has errors that are not correlated with errors in the original electron density map at x. Information from the electron density at points surrounding the point x is used to obtain a new estimate of the value of the electron density at x. One way to remove the information about the electron density at x would simply be to consider the electron density in a spherical shell around the point x. If the inner radius of the shell were large enough, then the values of electron density inside the shell would be relatively uncorrelated with the electron density at x. The choice of an inner radius, however, is not obvious because the electron density map is a Fourier sum of terms with widely varying spatial frequencies. Consequently, there is significant correlation between values of electron density at point x with points even as far away as the resolution of the map. Additionally, it is disadvantageous to exclude all density values close to x in the calculations because the patterns to be considered are very local.

An alternative method is to create a local density function for points near x with values that are similar to the electron density near x, but that are adjusted in such a way that the values are uncorrelated with the electron density at x. This modified local density $g_x(\Delta x)$ will depend on the coordinate difference $\Delta x$ between each point near x and x. The function $g_x(\Delta x)$ is a function of both x and $\Delta x$ and therefore must be calculated separately for each point x and offset $\Delta x$ in the map.

The value of the function $g_x(\Delta x)$ is desired to be generally similar to the value of the electron density at $x+\Delta x$, which is represented by $\rho(x+\Delta x)$. As $\Delta x$ is increased, $g_x(\Delta x)$ is desired to become very close to $\rho(x+\Delta x)$. That is, $$g_x(\Delta x) \approx \rho(x+\Delta x), \qquad (1)$$

$$g_x(\Delta x) \to \rho(x+\Delta x) \text{ for large } \Delta x. \qquad (2)$$

The function $g_x(\Delta x)$ should also be uncorrelated everywhere with the value of the electron density at x, given by $\rho(x)$. One way to specify this is to require that for any offset $\Delta x$, if the entire map is traversed and $g_x(\Delta x)$ is calculated for each point x, then $g_x(\Delta x)$ and $\rho(x)$ are to be uncorrelated:

$$\langle g_x(\Delta x)\rho(x)\rangle_x = 0 \;\forall \Delta x. \qquad (3)$$

Another desirable property of $g_x(\Delta x)$ for the current purpose is to have its value at $\Delta x=0$ be equal to the mean value of $g_x(\Delta x)$ for nearby points $\Delta x$. The method used below for comparing local patterns to a template is based on the correlation of densities. If the value of $g_x(\Delta x=0)$ were always set to 0, for example, then the mean value of local density would contribute to this correlation. A way to remove information about the mean value of local density is to specify the requirement that, $$g_x(\Delta x=0) = \langle g_x(\Delta x)\rangle_{\Delta x}, \qquad (4)$$

where all values of $\Delta x$ in the region to be used later in calculations of correlations of densities are considered in the averaging.

A function $g_x(\Delta x)$ 46 that has all these properties is, $$g_x(\Delta x) = \rho(x+\Delta x) - [\rho(x) - \langle \rho(x+\Delta x)\rangle_{\Delta x}] W(\Delta x), \qquad (5)$$

where the weighting function $W(\Delta x)$ is given by, $$W(\Delta x) = U(\Delta x)/[1 - \langle U(\Delta x)\rangle_{\Delta x}], \qquad (6)$$

and where the function $U(\Delta x)$ is the normalized value of the Patterson function near the origin, calculated from the electron density map itself using the relation, $$U(\Delta x) = \langle \rho(x)\rho(x+\Delta x)\rangle_x / \langle \rho^2(x)\rangle_x. \qquad (7)$$

In essence, $g_x(\Delta x)$ is then used 48 as a modified version of the electron density at $x+\Delta x$, after correction for the difference between $\rho(x)$, the value of the electron density at x, and $\langle \rho(x+\Delta x)\rangle_{\Delta x}$, the mean of nearby values, all using the weighting function $W(\Delta x)$. It can be verified by substitution that both Eqs. (3) or (4) are satisfied by this function. Additionally Eqs. (1) and (2) are satisfied because the normalized, rotationally-averaged Patterson function is normally quite small everywhere except near the origin and normally becomes very small for points far from the origin.

Local Pattern Identification (File resolve_pattern_2.05.f: subroutine local_pattern_setup (generation of a set of templates))

The first step in the procedure for density modification by pattern matching is to obtain templates that correspond to common patterns of local electron density. These patterns are generated using the local electron density near each point x in density-modified experimental electron density maps, modified to remove information from the central point x, as described for FIG. 3. The maps can be calculated at any resolution, but a set of templates is normally associated with a particular resolution (typically $d_{min}$=2.6 Å).

The approach used here to obtain templates 50 is hierarchical as described with reference to FIG. 4. First, three separate sets of $N_{max}$ (typically 40) templates are generated 52 using only points in an electron density map that have either low, medium, or high electron density. Then a subset (typically 40) of these templates that have low mutual correlation is selected, as determined below. Then an even smaller subset of $N_{final}$ (typically 20) templates is chosen 68 from this group in order to maximize the predictive power of the templates while maintaining a fixed number of total templates.

To generate a set of templates (File resolve_pattern_2.05.f: subroutine local_pattern_setup), each grid point in an electron density map is considered 52, one at a time, only including points that are associated with either low ($\rho<\overline{\rho}-0.8\sigma$), medium ($\overline{\rho}-0.2\sigma<\rho<\overline{\rho}+0.2\sigma$), or high electron density ($\overline{\rho}+1.5\sigma<\rho$), where $\overline{\rho}$ and $\sigma$ are the mean and standard deviation of the map, depending on the set of templates to be created. If the map used to generate templates corresponds to a crystal for which the protein structure is already known, then grid points that are more than a specified distance (typically 2.5 Angstroms) from the atom in the protein structure are typically excluded from the calculations, as the density near them is likely to be relatively uniform.

The grid points are the same that are conventionally used to calculate the electron density map. Typically, the grid spacing is ⅓ to ⅙th the resolution (Blundell and Johnson, 1976) of the X-ray data used to calculate the map. For each appropriate grid point (x) the modified local electron density $g_x(\Delta x)$ is calculated 56 as described below for all neighboring points within a radius $r_{max}$ (typically $r_{max}$=2 Å when $d_{min}$=2.6 Å). This modified electron density is compared 58 to all existing templates using the correlation coefficient of density in the template with the modified local density as a measure of similarity. For each existing template, $N_{rot}$ different rotations of the template are considered so as to attempt to match the modified local density in any orientation, and the highest correlation coefficient, as defined above, of the match for all rotations of the template is noted. In the examples considered here, a total of $N_{rot}$=158 rotations was used to sample the possible 3D rotations of an object with a rotation of about 50° relating neighboring orientations.

If the correlation coefficient of the local modified electron density at this point x with an existing template k is greater than $CC_{min}$ (typically $CC_{min}$=0.85), then the local modified density at this point is included 60 in the definition of template k by rotating the density to match the current template k. To include the local modified density at this point in template k, the local modified density is rotated to match the orientation of template k. Then template k is modified to include all the previous contributions to template k as well as the rotated local modified density. The new value at each grid point in template k is the average of the values of this grid point in this and all previous versions of rotated local modified density that contribute to template k. If the local modified electron density does not have a correlation with any existing template greater than $CC_{min}$, then the local modified density 62 is used to start a new template. Once $N_{max}$ templates have been created (typically $N_{max}$=40) then the local modified density at each subsequent point is included in whichever template with which it has the highest correlation coefficient after rotation.

By repeating the generation of templates using points in the electron density map that have low, medium, and high density, a relatively diverse set of templates is created 64. Next, a subset (typically ⅓) of these is chosen (File resolve_pattern_2.05.f: subroutine read_pattern (read in a set of patterns and select a subset N of these patterns with minimal mutual similarity)) based on mutual correlation coefficients in order to have a set of templates 66 with the minimum possible similarity to each other. To do this, the correlation coefficients of all pairs of templates are calculated, and the template with the highest correlation to another template is eliminated. The process is repeated until the desired number of templates is obtained. The final selection of templates based on predictive power is carried out after analyzing the statistics associated with each of the $N_{max}$ templates obtained at this stage, as described below.

Statistics of Local Patterns—General Approach (FIG. 5)

(File resolve_pattern_2.05.f: subroutine local_pattern_setup; files analyze_tabulate.f and tabulate.f)

The second overall step in this process is to identify the relationships between the correlation of each template with local modified density in a map, and the value of the electron density at x. This is done for known maps both with and without added errors. There are many possible ways to describe these relationships, but a simple approach is used here to break it down into two parts.

The first part consists of an examination 90 of the statistics of high-quality known maps. Suitable maps are electron density maps that have already been used to determine a protein structure and that have a "figure of merit" (based on cos(phase error), Blundell and Johnson, 1976) of higher than about 0.75. At each point x in a high quality map, the two templates k, l are identified 92 that have the highest and next-highest correlation coefficients, respectively, with the local modified density at x (after rotation to maximize this value). Surprisingly, the electron density at a point x in a map is quite strongly dependent on these two templates k and l. That is, for electron density maps of proteins, the probability distribution $p(\rho|k, l)$ can be very informative about the electron density $\rho$ at x. Histograms are constructed 94 by tabulating the value of the (unmodified) electron density $\rho(x)$ as a function of k and l. The histograms are normalized 96 to yield an estimate of the probability distribution, $p(\rho|k,l)$ The second part is to consider the relationship between maps with and without added errors. (File tabulate.f) The approach is to begin with the observed correlation coefficients of all the templates at a point x to a map that contains errors, and then to use these, as described below, in a calculation of the probability that a particular pair of templates k and l would have the highest two correlation coefficients in the corresponding high-quality map. In this case, the statistics of density for the high-quality maps $p(\rho|k, l)$ obtained above can then be applied.

To carry out this process, a second set of probabilities are needed. The statistics analyzed above describe the properties of a high-quality map. In practice, the electron density map that is to be improved is not of high quality. It is necessary therefore to define the relationship between the statistics of a high-quality map and those of a lower-quality map. To do this, the probabilities $p(cc_k|cc_{obs,k})$ are calculated (File tabulate.f) that the correlation coefficient for template k to a point x in a high-quality map would have the value $cc_k$, given the observation that this template has a correlation coefficient of $cc_{obs,k}$ to the same point in a map with additional errors (FIG. 6, step 100). To account for differing levels of error in the experimental map, these probabilities are tabulated as a function of the overall figure of merit of the map with errors To apply these probability distributions to data near the point x in a new ("observed") electron density map (File resolve_pattern_2.05.f: subroutines get_load_cc and analyze_cc_hist), the correlation coefficient of each template k to the local modified density near x is first determined (once again, after trying many rotations and choosing the one for each template that maximizes the correlation coefficient). This set of correlation coefficients, $\{cc_{obs}\}$, and the two probability distributions $p(\rho|k, l)$ and $p(cc_k|cc_{obs,k})$ can then be combined as follows to obtain an estimate of the electron density $\rho$ at x in a high-quality version of the same map.

If it was known which two templates, k and l, have the highest correlation coefficients to the local modified density near x in a high-quality version of the new "observed" map, then the probability distribution, $p(\rho|k, l)$, could be used directly to estimate the probability distribution for $\rho$. The identity of k and l is not known, but suppose instead that the probabilities, $p(k,l|\{cc_{obs}\})$ were known for each possible pair, k and l, based on the correlation coefficients observed for the "observed" map. Combining these, $$p(\rho|\{cc_{obs}\})=\Sigma p(\rho|k,l)p(k,l|\{cc_{obs}\}), \qquad (8)$$

(File resolve_pattern_2.05.f: subroutines analyze_cc_hist and get_p_highest)

where the sum is over all possible pairs of templates k and l. An estimate of the electron density at x can then be obtained from the weighted mean, $$\rho_{est}=\int \rho p(\rho|\{cc_{obs}\})d\rho \qquad (9)$$

(File resolve_pattern_2.05.f: subroutines analyze_cc_hist and get_p_highest)

The probability, $p(k,l|\{cc_{obs}\})$, that the pair, k and l have the highest correlation coefficients to the local modified density near x in a high-quality version of the "observed" map can in turn be estimated from the observed correlation coefficients of all the templates to this map, $\{cc_{obs}\}$, in several steps. The probability is separated into two parts, one for the probability that template k has the highest correlation, and one for the probability that template l has the next-highest, given that template k has the highest correlation:

$$p(k,l|\{cc_{obs}\})=p(l|k,\{cc_{obs}\})p(k|\{cc_{obs}\}). \qquad (10)$$

(File resolve_pattern_2.05.f: subroutines analyze_cc_hist and get_p_highest)

The probability that template k has the highest correlation with the (non-existent) high-quality version of the "observed" map is now estimated. The correlation of template k with the high-quality map is integrated over all possible values of $cc_k$. For each value of $cc_k$, the probability is calculated that this is indeed the value of the correlation of template k, given by $p(cc_k)=p(cc_k|cc_{obs,k})$, and the probability that all other templates have a correlation coefficient less than $cc_k$ $$p(k|\{cc_{obs}\})=\int p(cc_k)\Pi_{j\neq k}p(cc_j<cc_k)dcc_k, \qquad (11)$$

(File resolve_pattern_2.05.f: subroutines analyze_cc_hist and get_p_highest)

where the integral is over all values of $cc_k$. The probability that template l has the next-highest correlation is given by, $$p(l|k,cc_{obs})=\int p(cc_l)\Pi_{j\neq k,l}p(cc_j<cc_l)dcc_l. \qquad (12)$$

(File resolve_pattern_2.05.f: subroutines analyze_cc_hist and get_p_highest)

Statistics of Local Patterns—Tabulating Histograms (File tabulate.f)

An important part of this step consists of generating histograms of values (FIG. 6) for the electron density at x (File tabulate.f), as a function of the correlation coefficients of the $N_{max}$ templates with the local modified density at x, as described below. Each of the $N_{max}$ templates is compared to the modified local density at all points in a set of high-quality maps. A suitable set of maps would include proteins of varying local structure (alpha-helices, strands, turns, and the like). A "high-quality" map is a map is a map having a high estimate of phase accuracy, e.g., a figure of merit defined by a cos(phase error)>0.75. At each point x, the two templates k and l that have the highest and next-highest correlation coefficients, respectively, with the local modified density at x are identified (after rotation to maximize this value). Then the value of the (unmodified) electron density $\rho(x)$ is tabulated as a function of k and l. These histograms are then normalized to yield an estimate of the probability distribution, $p(\rho|k, l)$.

The second part of this step is to obtain probability distributions (File tabulate.f), $p(cc_k|cc_{obs,k})$, relating 100 the correlation coefficient value, $cc_{obs,k}$, observed for a particular template at a point x in a map that contains added errors to the correlation coefficient, $cc_k$, that would be observed for the identical template at the identical point x in the corresponding map without any added errors. These probability distributions are calculated by using paired sets of high-quality experimental maps with and without added errors 102. At each point in a map, the correlation coefficient of each template k to the map without added errors, $cc_k$, and the correlation to the map with added errors, $cc_{obs,k}$, are noted 104. This results in a set of histograms consisting of the number of times in these maps $n(cc_k, cc_{obs,k})$ that the correlation coefficient in the high-quality map is $cc_k$ and the correlation coefficient in the map with errors id $cc_{obs,k}$. Normalization 106 of the resulting histograms leads to an estimate of the probability, $p(cc_k|cc_{obs,k})$, that $cc_k$ is the correlation to the map without added errors if the value $cc_{obs,k}$ is observed in the map with added errors.

This calculation is repeated 108 for maps with varying levels of additional errors by creating simulated phase sets with Gaussian distributions of phase errors (File resolve_pattern_2.05.f: subroutine randomize_phases) with varying overall values of the cosine of phase error, $<\cos \Delta\phi>$, ranging typically from 0.5 to 0.8. In application to a new "observed" map, the probability distribution obtained using data with added phase errors with a mean cosine $<\cos \Delta\phi>$ similar to the figure of merit of the experimental map is used.

Figure 7:
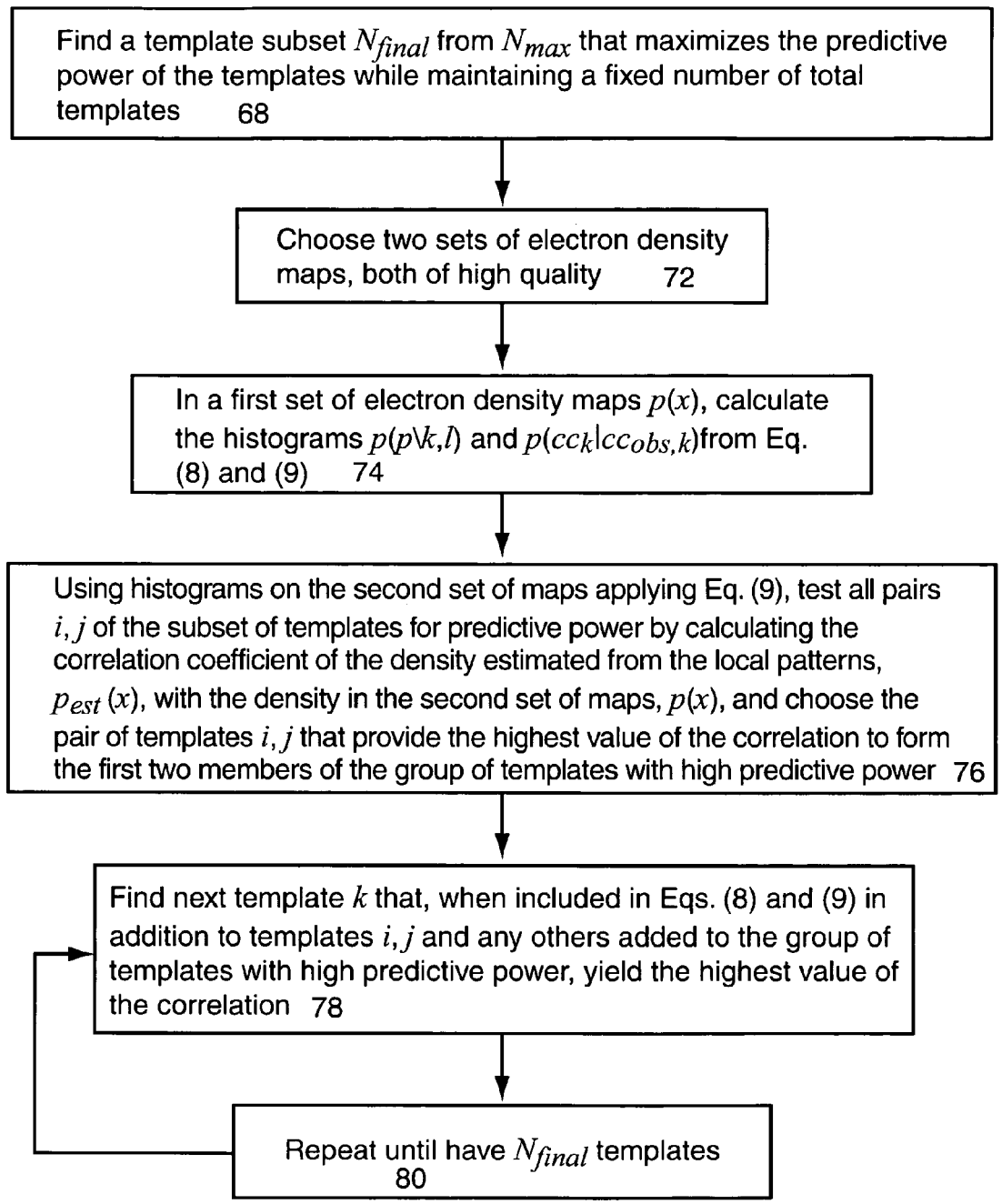
FIG. 7 is a flow diagram for finding a final subset of templates that maximize the predictive power of the templates.

Selection of Templates Based on Predictive Power (Reference FIG. 7)

(File analyze_tabulate.f)

The final selection of $N_{final}$ templates is based on predictive power. A subset of $N_{final}$ templates is selected 68 from the $N_{max}$ templates obtained earlier using high-quality electron density maps. The subset is selected to maximize the correlation between the electron density calculated using Eq. (9) and the electron density in the maps. Two sets of electron density maps are selected 72. The histograms that form the basis of Eq. (9) are calculated from experimental density for one set of the maps, and the correlation is calculated for another. Using histograms on the second set of maps, applying Eq. (9) 76, all pairs i, j of the templates are tested for predictive power. The correlation coefficient is calculated of the density estimated from the local patterns, $\rho_{est}(x)$, of the first set of maps with the density in the second set of maps. The pair of templates i, j that yields the highest correlation is first identified to form the first members of the group of templates with high predictive power. Next, the next template k that, when included in Eqs. (8) and (9) with templates i, j, increases the highest value of the correlation is found. Then, one by one, the templates that increase this correlation by the largest amount is added 80 to the group, until $N_{final}$ templates are chosen.

Indexing the Rotations for Each Template to Reduce Computational Requirements (File resolve_pattern_2.05.f: subroutines get_index and match_pattern_direct_list)

The slowest step in applying the procedures described here consists of calculating the maximum correlation of local modified density with each of the $N_{final}$ templates, considering as many as 158 rotations of each template (or local density) for each point. We have developed a simple indexing system that reduces the number of rotations that need to be considered for each template.

The index for a point x is based on the density at M points near x (typically M=9). Point m is given an local index $i_m$ from 0 to 3, based on the local density at that point ($\rho \leq \sigma$; $-\sigma < \rho \leq 0$; $0 < \rho \leq \sigma$; or $\rho > \sigma$), ordered 0, 1, 2, and 3, where $\sigma$ is the r.m.s. of the entire map. Then an overall index l is calculated for the local density from the relation, $$l = \Sigma i_m 4^{(m-1)} \qquad (13)$$

(File resolve_pattern_2.05.f: subroutine get_index)

where the sum is over the M nearby points.

Next, the relationship between the index l and the best rotation is tabulated (File resolve_pattern_2.05.f; subroutine get_local_cc; file index_setup.f) for each of the templates using high-quality experimental maps containing added errors. For each point in each map used above to calculate statistics of the correlation of templates with local modified density, the index l is calculated and the optimal rotation is noted for each template. Then an indexing table is constructed, in which each index l is associated with a list of preferred rotations for each template. The table is constructed so that about 95% of the time, the optimal rotation for a given template is contained in the list. This indexing procedure reduces the number of rotations that need to be considered by about a factor of 5. Other indexing methods could be applied that might further reduce the number of rotations to be considered (e.g., Funkhouser, et al., 2003).

Figure 8:
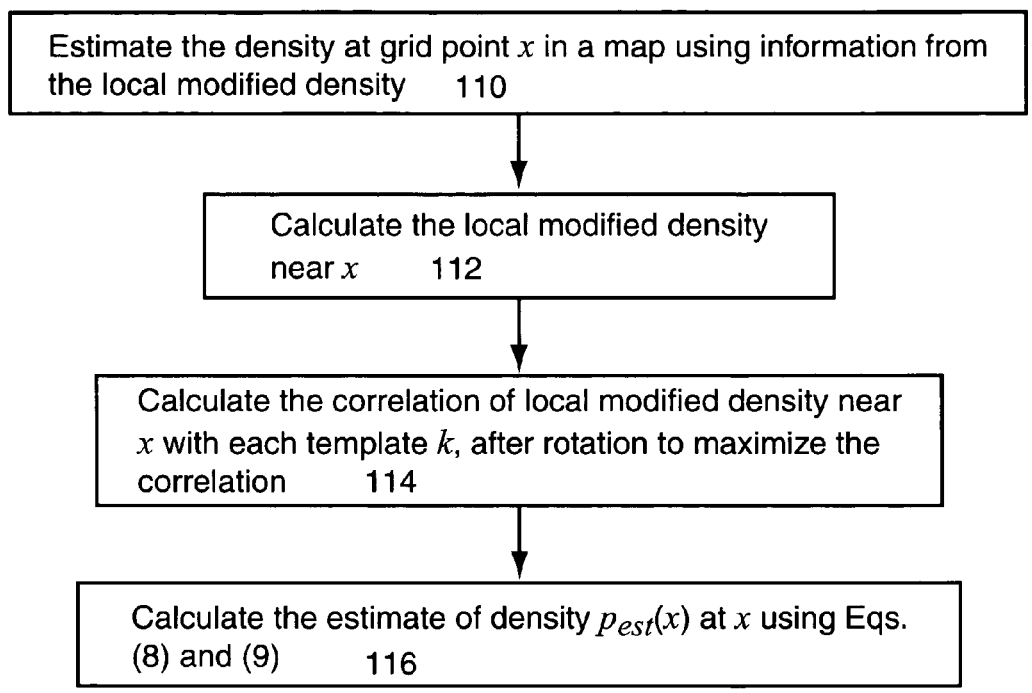
FIG. 8 is a flow diagram for estimating the density at a specific grid point in a map using information from the local modified density.

Using Local Patterns to Create a New Estimate of Electron Density (FIG. 8, Step 110)

(File resolve_pattern_2.05.f: subroutine get_local; file index_setup.f)

The local modified density 112 near a point x in an electron density map can be analyzed 114 using Eq. (8) to produce a probability distribution, $p(\rho|\{cc_{obs}\})$, for the electron density at x. The estimate from Eqs. (8) and (9) of density at x, $\rho_{est}$, (and the uncertainty in this estimate, $\sigma_{st}$, if desired) is then used 116 to construct a new estimate of the electron density in the map (File resolve_pattern_2.05.f: subroutine get_local; file index_setup.f). This "recovered image" of the electron density map can be visualized with or without smoothing, or it can be used as a target for statistical density modification (Terwilliger, 2000), or it can be combined directly by a multiplication of phase probability distributions with the original electron density map to obtain an improved map.

Using Statistical Density Modification to Estimate Phases Based on a Target Electron Density Function Statistical density modification (Terwilliger, 2000) is a procedure for calculating crystallographic phase probabilities based on the agreement of the map resulting from these phases with prior expectations. Any set of prior expectations about the map can be included in this procedure. In particular, if an estimate of electron density is available for all points in the map (e.g., the recovered image obtained in the procedure described above), then this estimate can be used as prior information about the map. In this procedure, observed values of the amplitudes of structure factors are used, and an estimate of uncertainty in the electron density is required. This procedure is used to estimate phase probabilities from a recovered image, where the expected electron density is simply the best estimate from Eq. (9), and the uncertainty is taken to be a constant everywhere, given by the root mean square of a map calculated with the observed structure factor amplitudes.

RESULTS AND DISCUSSION

Removing Information About Electron Density at x From the Local Electron Density An important aspect of the pattern matching density modification method presented here is that it is designed to yield an estimate of the electron density that has errors uncorrelated with the errors in the original map. This is accomplished by using only information from the region around a point x to estimate the density at x, and not including any information about the density at x in the process, as described in Methods. FIGS. 9A and 9B illustrate this process of removing information about electron density at x. FIG. 9A shows a section of a density-modified MAD electron density map for initiation factor 5A (IF5A; Peat et al., 1998) in the region near a particular point x (the point x is designated by a star at the center of the figure). Note that the density at x is positive in this case. In FIG. 9B, the density is adjusted to remove the information about the density at x from x and from all neighboring points. This calculation essentially consists of subtracting the origin of a normalized Patterson function corresponding to this map, multiplied by the value of the density at x minus the mean local density, from all neighboring points, as described in Methods. This calculation has the effect of setting the value of the density at x to the mean density in the local region, setting the density very near x to intermediate values, and leaving the value of points far from x unchanged.

Common Local Patterns in Protein Electron Density Maps

The analysis of local patterns in electron density maps was carried out using the density modified MAD electron density map from IF5A, calculated at a resolution of 2.6 Å (PDB entry 1BKB; Bernstein et al., 1998; Peat et al., 1998). This was a very clear map with a correlation coefficient to the map calculated from the final refined model of IF5A of 0.82. Local patterns were analyzed for regions centered on each point in this grid, considering only points within 2.5 Å of an atom in the model. Local patterns were identified as described in Methods using the modified local density surrounding each point. This approach removes information about the density at x from the nearby density. The patterns are selected after considering rotations about the central point, so any rotational differences between templates are not significant in determining their features.

The final templates were chosen on the basis of their predictive power. The $N_{max}$=40 templates that were initially created using the model electron density map for IF5A were then compared to all points in two other density-modified experimental electron density maps, the armadillo repeat of β-catenin (Huber et al, 1997) and red fluorescent protein (Yarbrough et al., 2001) and correlation coefficients for each template at each point were obtained. Then the same 40 templates were compared in the same way with the IF5A map. Finally, subsets of the 40 templates were considered. For each subset of templates, the β-catenin and red fluorescent protein electron density maps were used to generate histograms, and the IF5A map was used to compare the estimates of electron density obtained using Eq. (9) with IF5A electron density. In the first cycle of identifying templates, all pairs of templates were considered, and the pair yielding the highest correlation was chosen. In subsequent cycles, the additional template that yielded the greatest improvement in correlation was chosen. FIG. 10, open circles, shows the correlation of estimated and model density as a function of the number of templates used. Much of the information is contained in just two templates, and almost all the rest in the first 20. Based on this observation, we have used 20 templates for the remainder of this work.

The fundamental property of macromolecular electron density maps that is used in our approach is that different local patterns of density in these maps are associated with different values of the density at their central point. The open circles in FIG. 10 shows that such an association exists and that only a small number of templates are needed to describe it. We next tested whether a similar association exists for random maps. The closed triangles in FIG. 10 were obtained in the same way as the open circles, except that all the maps were calculated after randomizing all the crystallographic phases. The closed triangles in FIG. 10 show that there is essentially no association between local patterns of density and density at their central points for the random maps. This means that the correlations between patterns and densities at their central points is a feature of protein-like maps, and not a feature of maps with random phases.

Figure 11:
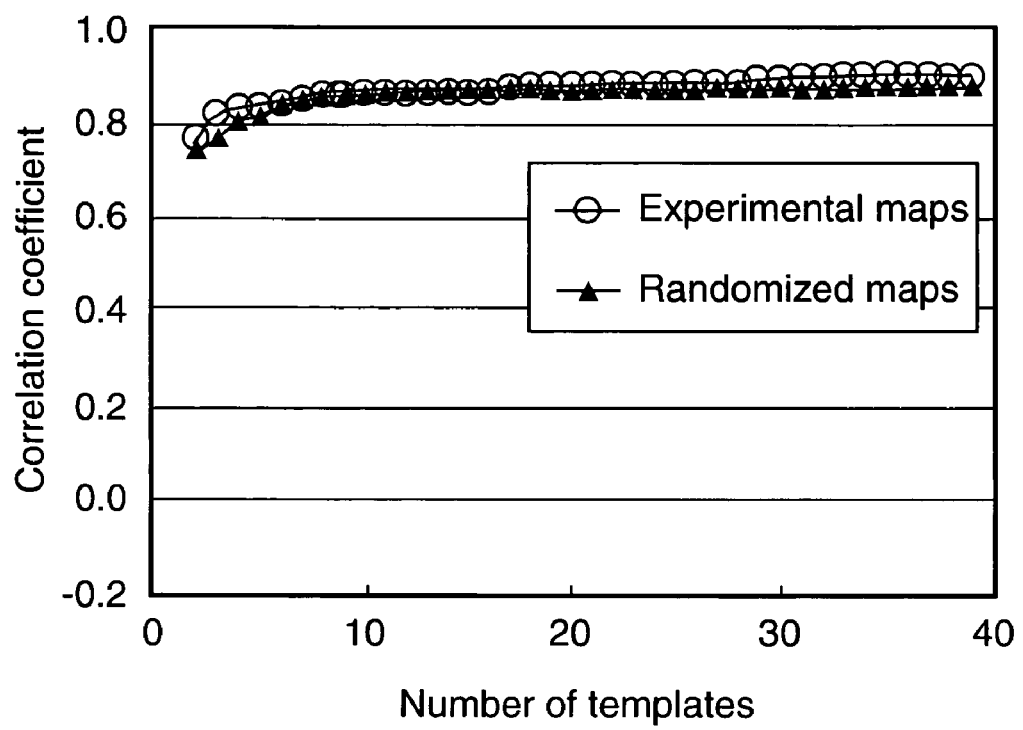
FIG. 11 graphically illustrates in comparison with FIG. 10 that removal of information about the density at a point in the analysis of the patterns surrounding the point since the local density was adjusted in FIG. 10 to remove the point density information, but not for FIG. 11.

An important part of the present approach was the removal of information about the density at a point x in the analysis of the patterns surrounding x using Eq. (5). The reason for doing this was to obtain an estimate of the density at point x that is independent of the current value of density at that point. FIG. 11 shows that this choice of methods is also important for discriminating between patterns that are due to noise and those that are due to protein-like features. FIG. 11 was calculated in exactly the same way as FIG. 10, except that the local density was not adjusted to remove information about the value of the density at the central point, and a completely new set of templates and statistics was used, reflecting this different approach. This was accomplished by not applying Eq. (5) to the local density. The open circles in FIG. 11 show that if the local density is not adjusted to remove information about the central point, then templates can be obtained that give a very high correlation between the value of the density calculated from Eq. (9) and the actual density. However, this correlation is likely to be almost entirely due to the fact that information about the central point is included in both the templates and the correlations. Supporting this interpretation, the closed triangles in FIG. 11 show that randomized maps give essentially the same correlations as protein electron density maps when the information about the central point is not removed from the calculations.

Figure 12A:
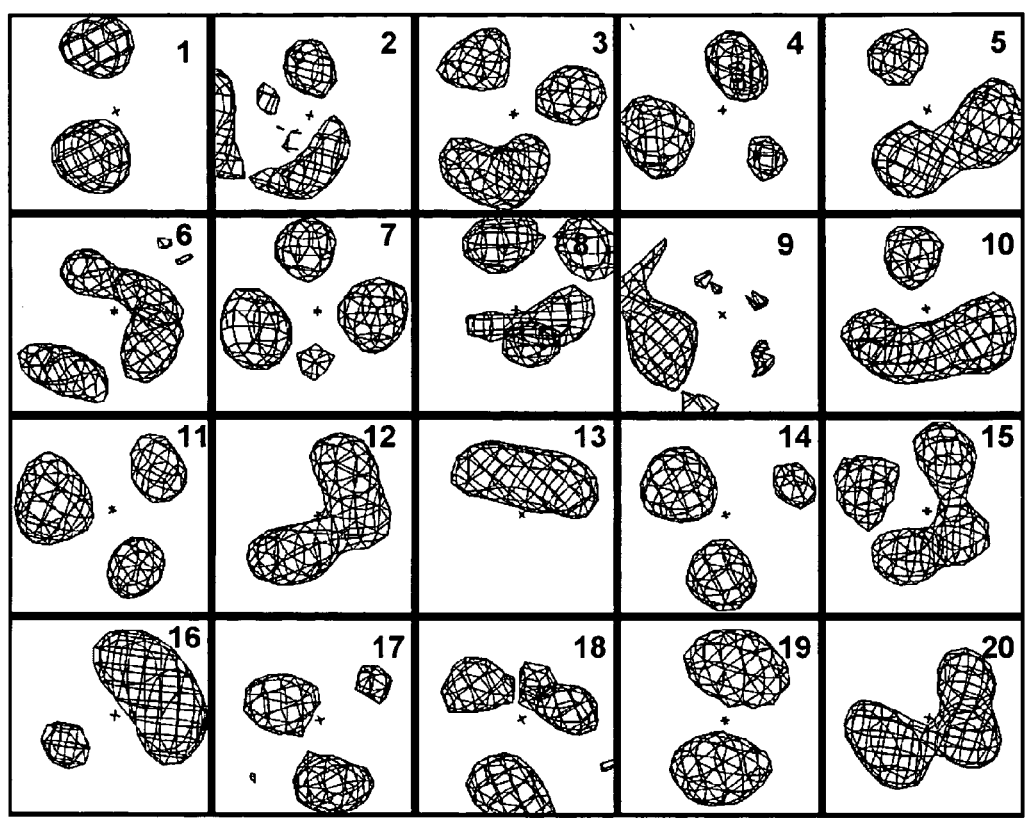
FIGS. 12A and 12B graphically depicts a set of templates created in accordance with the present invention arranged in order of decreasing contribution to the estimates of density.

FIG. 12A shows contours of positive density corresponding to the $N_{max}$=20 templates obtained. The templates are arranged in order of decreasing contribution to the estimates of density. The patterns are very simple, typically containing one to three spherical or extended regions of positive density and one or more rings or regions of negative density (adjusted map density values so that the overall mean density in the map is zero) in various relations to the central point. Some of the pairs of templates are similar (for example #17 and #18) and as shown in FIG. 11, the number could be reduced further with just a small reduction in predictive power.

The core of the method described here is the association of different templates with different expected values of electron density at the point that is at the center of the templates. The electron density near a point x in a map (typically within 2 Angstroms) is compared with the 20 templates, and the two templates that match the density most closely are identified. The procedure is first done with high-quality experimental maps to associate pairs of templates with expected density, and then with an observed map to estimate the values of electron density in high-quality version of the observed map. In order to use as much information as possible, the process is carried out in a probabilistic fashion, considering the possibility that any pair of patterns might best match the density in a high-quality version of the observed map.

The 20 patterns are each associated with different average values of density at their central points. For example, template #1 contains two spherical regions of positive density situated approximately equidistant from the origin and on opposite sides of the origin. At locations where this pattern is the one that best matches the density in model maps, the mean density at the central point is about −0.3+/−0.6 (on an arbitrary scale with the mean of the map equal to zero). Template #12 contains a curved lobe of positive density immediately adjacent to the origin. Template #12 is associated with mean density of about 0.6+/−0.9. Table I lists the density associated with locations where each of the 20 templates best match the local modified density in model maps.

TABLE I

| Template | Mean density at center (arbitrary units, with mean of map equal to zero) | Variance of mean density |
|---|---|---|
| 1 | −0.29 | 0.60 |
| 2 | 0.06 | 0.73 |
| 3 | −0.63 | 0.59 |
| 4 | −0.55 | 0.60 |
| 5 | −0.38 | 0.81 |
| 6 | 0.49 | 0.95 |
| 7 | −0.68 | 0.56 |
| 8 | −0.05 | 0.72 |
| 9 | −0.40 | 0.55 |
| 10 | −0.32 | 0.70 |
| 11 | −0.41 | 0.74 |
| 12 | 0.62 | 0.87 |
| 13 | 0.37 | 0.72 |
| 14 | −0.46 | 0.66 |
| 15 | 0.46 | 1.00 |
| 16 | −0.17 | 0.76 |
| 17 | −0.03 | 0.78 |
| 18 | −0.15 | 0.66 |
| 19 | −0.27 | 0.81 |
| 20 | 0.49 | 1.00 |

Reconstructing Model Electron Density Using Correlations with Local Patterns

Figure 12B:
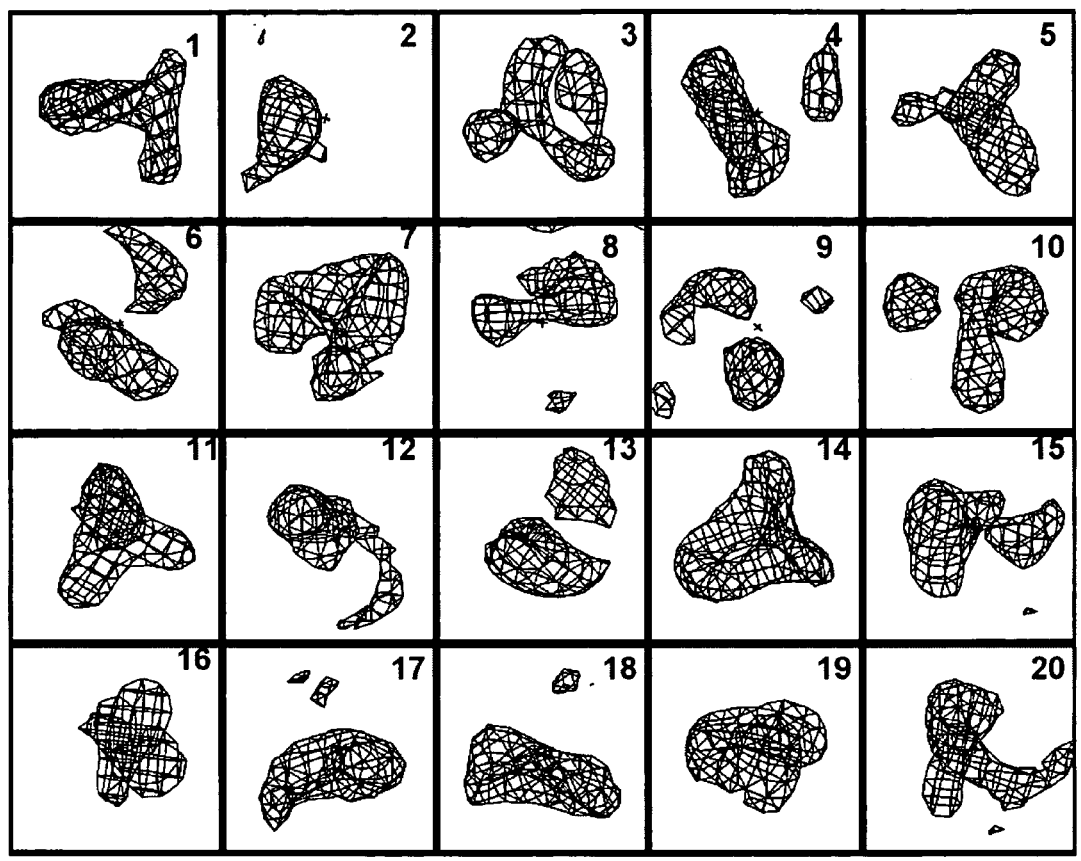

The templates shown in FIGS. 12A and 12B and the density typically associated with them listed in Table I can be used to reconstruct an image of an electron density map.

Figure 13:
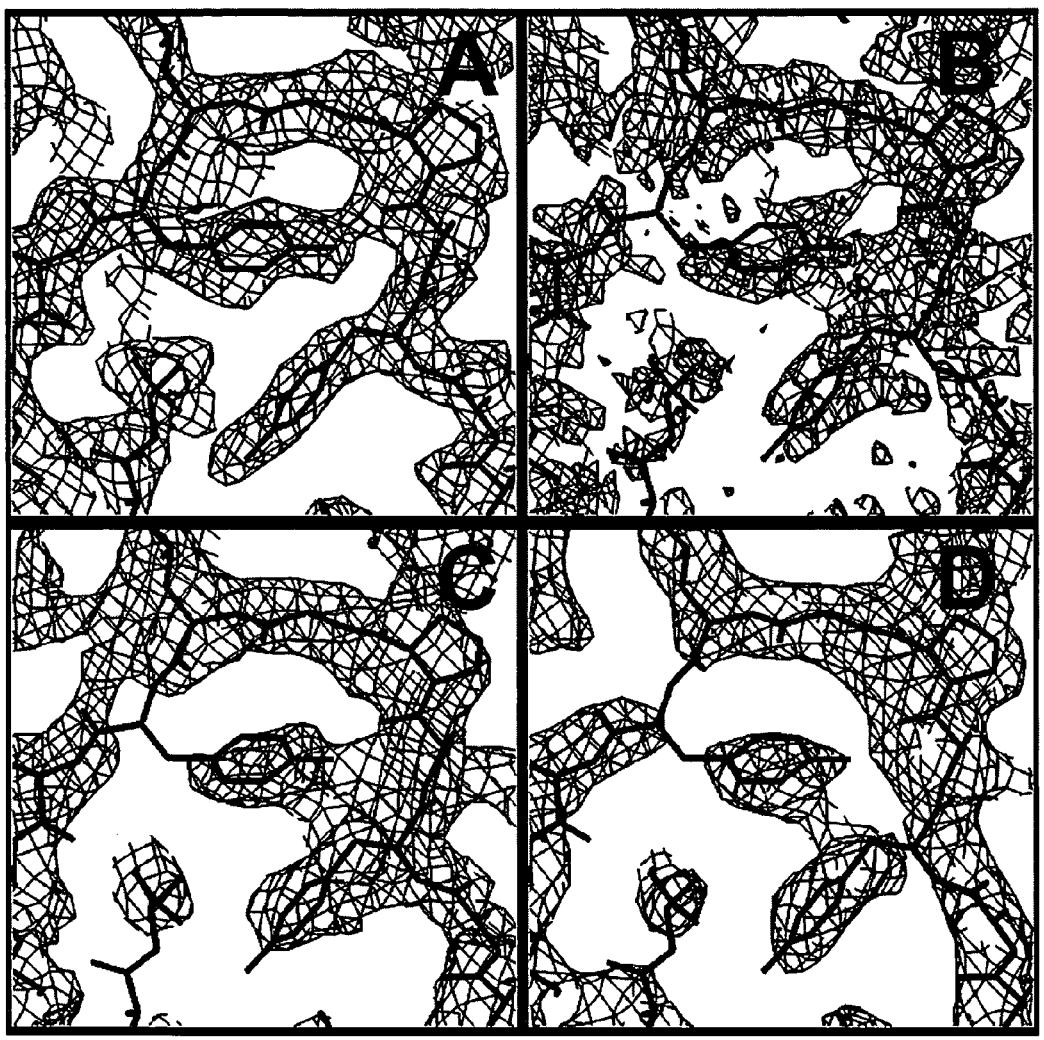
FIG. 13, Panels A–D, show the electron density map modified in successive stages according to the process of the present invention.

FIG. 13, Panels A–D, shows an example using model data so that errors can be readily analyzed. Panel A shows a section of model electron density with errors calculated using the structure of gene 5 protein (PDB entry 1VQB; Skinner et al., 1994) at a resolution of 2.6 Å. The errors in the phases were adjusted so that the map had a correlation coefficient to the perfect map of 0.81. The estimated electron density reconstructed from this map is shown in Panel B, and a version of this density, smoothed with a radius of 1.5 Å, is shown in Panel C. Finally, phases were estimated using statistical density modification based on the model structure factor amplitudes the reconstructed density (Panel D). The reconstructed density has a correlation coefficient to the original (model) map of 0.19; the smoothed image has a correlation of 0.38, and the map calculated with phases obtained from the reconstructed density and model amplitudes has a correlation coefficient of 0.46.

As model data were used to obtain the images in FIG. 13, it is possible to analyze the errors in the recovered image and determine whether they are in fact independent of the errors in the original map. The errors in electron density maps are somewhat complicated as they come from errors in phase angles. A simplified error model in which the values of the electron density in two maps $y_1(x)$ and $y_2(x)$ have correlated errors is assumed for the present analysis. For convenience in this analysis the maps $y_1(x)$, $y_2(x)$ and $t(x)$ each are normalized to an rms value of unity and a mean of zero. In this error model, each map has a component that is related to $t(x)$, the true density in a perfect map (also normalized in the same way), each map has a component, $c(x)$, that is an error term unrelated to $t(x)$ but that is the same in the two maps, and each map has an independent error term, $e_1(x)$ and $e_2(x)$. As this is model data, we know the values of $t(x)$ as well as the values of $y_1(x)$ and $y_2(x)$.

$$y_1(x) = \alpha_1 t(x) + c(x) + e_1(x) \tag{13}$$

$$y_2(x) = \alpha_2 t(x) + c(x) + e_2(x) \tag{14}$$

In this model case the coefficients $\alpha_1$ and $\alpha_1$ can be estimated from the known maps $t(x)$, $y_1(x)$ and $y_2(x)$ $$\alpha_1 \cong \langle y_1(x) t(x) \rangle \tag{15}$$

$$\alpha_2 \cong \langle y_2(x) t(x) \rangle. \tag{16}$$

Then we can estimate the correlation of errors $cc_{errors}$ with the relation, $$cc_{errors} \cong \langle [y_1(x) - \alpha_1 t(x)][y_2(x) - \alpha_2 t(x)] \rangle / \{\langle [y_1(x) - \alpha_1 t(x)]^2 \rangle \langle [y_2(x) - \alpha_2 t(x)]^2 \rangle\}^{1/2} \tag{17}$$

Using Eq. 17 we find that the correlation coefficient of the errors in the starting map with errors with the errors in the recovered map in Panel B is −0.01. The same calculation for the recovered, smoothed map in Panel C, leads to a correlation coefficient of the errors of −0.02. Similarly, the calculation for the map in Panel D obtained using phases calculated from the recovered image and model amplitudes lead to a correlation of errors of −0.04. This indicates that the errors in the recovered image are not correlated with the errors in the original map.

We have found that the independence of errors is not as perfect when density-modified phases are used. To examine this, we started with model phases and amplitudes, introduced errors into the phases, leading to an electron density map with a correlation to the perfect map of 0.6, and then carried out statistical density modification on this map (not including any local pattern information), leading to a density-modified map with a correlation to the perfect map of 0.83. Then this density-modified map was analyzed for local patterns as described above. In this case the smoothed, recovered image had a correlation to the perfect map of 0.50. The correlation of errors with the density-modified map was 0.21, considerably higher than in the case where the map used for pattern identification had completely random errors. This suggests that the method might not be quite as effective when used on density-modified maps as on experimental maps.

Figure 14:
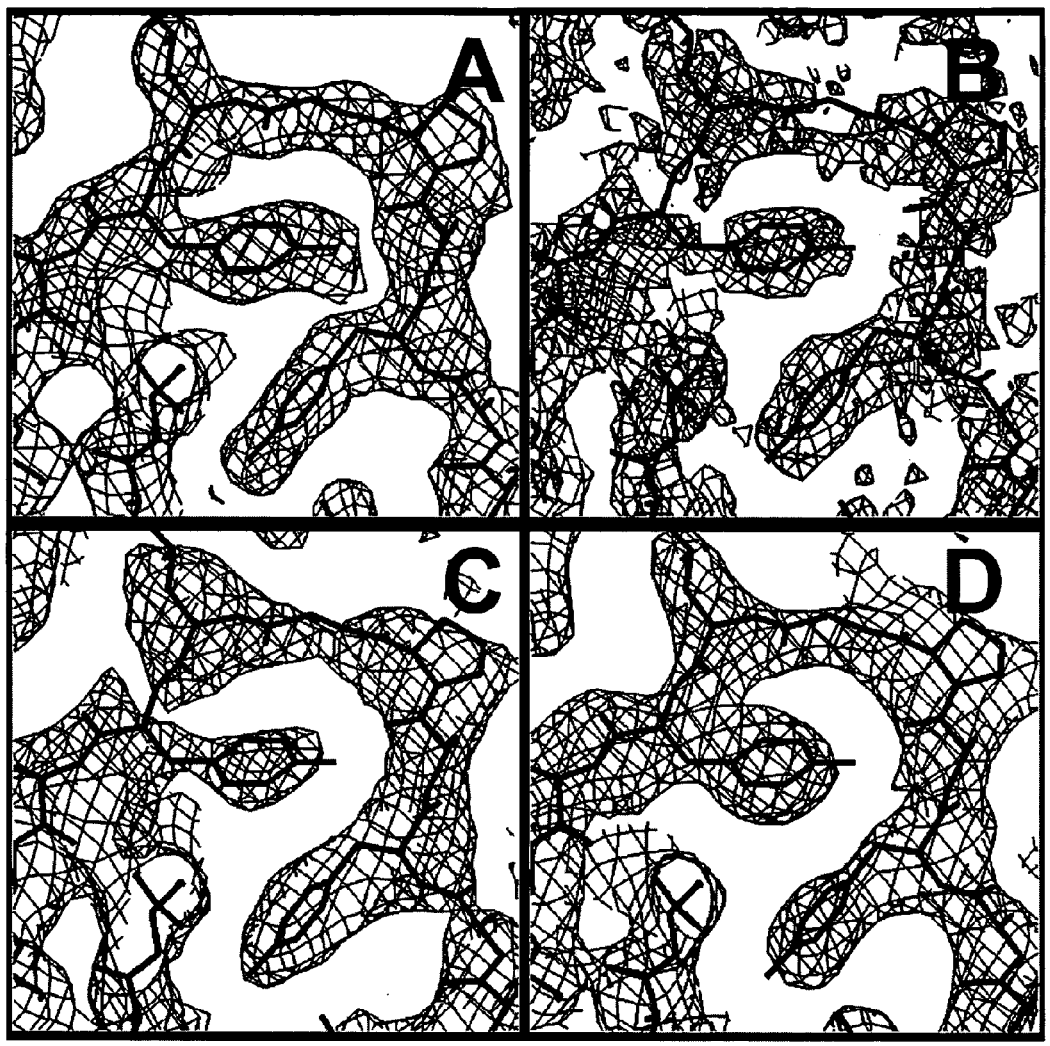
FIG. 14, Panels A–D illustrates the application of the process to modifying 3-wavelength MAD data on gene 5 protein.

Reconstructing Electron Density From Density-modified Experimental Maps Using Correlations with Local Patterns The analysis described above was carried out with electron density calculated from models so that the error analysis could be done in detail. We next applied the method to electron density obtained from a MAD (multiwavelength anomalous diffraction) experiment so that its utility with real data could be examined. The electron density obtained after applying statistical density modification (Terwilliger, 2000) to 3-wavelength MAD data on gene 5 protein (PDB entry 1VQB; Skinner et al., 1994) was used as the starting point for this analysis. This RESOLVE electron density map had a correlation coefficient of 0.79 to the model density calculated from PDB entry 1VQB. Referring to FIG. 14, Panels A–D, Panel A shows a section through this density-modified map. Local pattern analysis was applied to this map as described above. Panel B shows the image that was recovered from this map, Panel C shows a smoothed version of this image, and Panel D shows the map obtained using phases calculated from the recovered image and observed structure factor amplitudes. The recovered image in Panel B has a correlation of 0.25, the smoothed recovered image in Panel C has a correlation of 0.42, and the map calculated using phases from the recovered image in Panel D has a correlation of 0.52.

Figure 4:
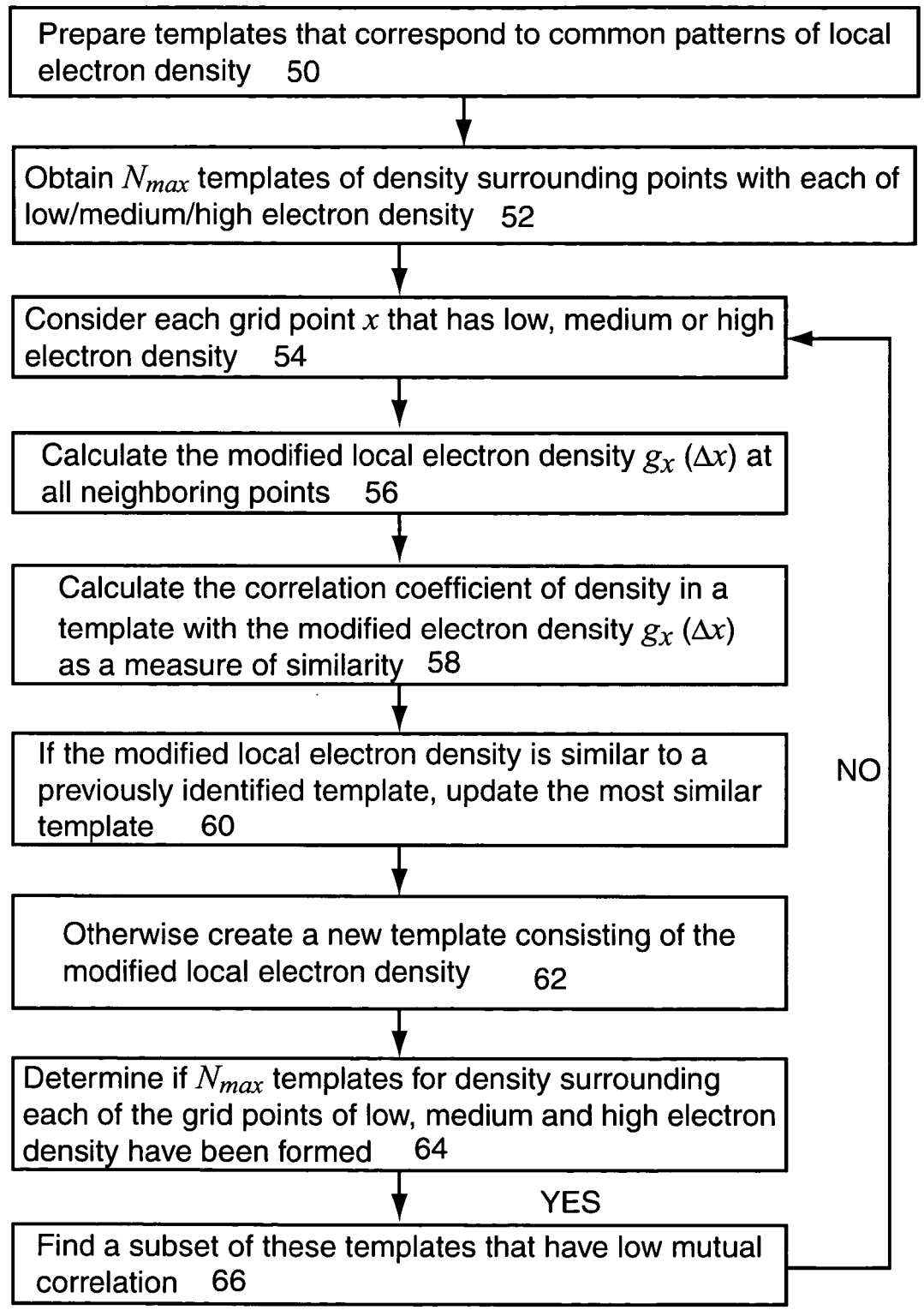
FIG. 4 is a flow diagram for preparing templates that correspond to common patterns of local electron density.

An approximate version of the error analysis described in the previous section for FIG. 4 was carried out for the maps in FIG. 14. In this analysis the "true" density was taken to be the density calculated from the model of gene 5 protein (PDB entry 1VQB). The correlation of errors between the starting RESOLVE map in Panel A with the errors in the recovered image in Panel B was 0.15, and the correlation of errors between the starting RESOLVE map with the errors in the smoothed recovered image in Panel C was 0.23. The correlation of errors in the map calculated using phases from the recovered image in Panel D with the errors in the starting RESOLVE map was 0.36. This means that the errors are not highly correlated in this analysis, but that they are also not completely independent. Part of the correlation of "errors" could be due to the fact that the "true" density is not known, and the errors are estimated using model density for gene 5 protein. Consequently any errors in this model density would lead to correlation of "errors" in all the maps in this analysis.

Combination of Phase Information From Local Pattern Identification with Experimental Phase Information FIG. 14, Panel D, showed an electron density map calculated using observed structure factor amplitudes for gene 5 protein, and phase probabilities obtained using statistical density modification on the reconstructed image in Panel B. These phase probabilities were then combined with the original phase probabilities from the 3-wavelength MAD experiment to yield a set of phase probabilities, and a new electron density map.

Figure 15:
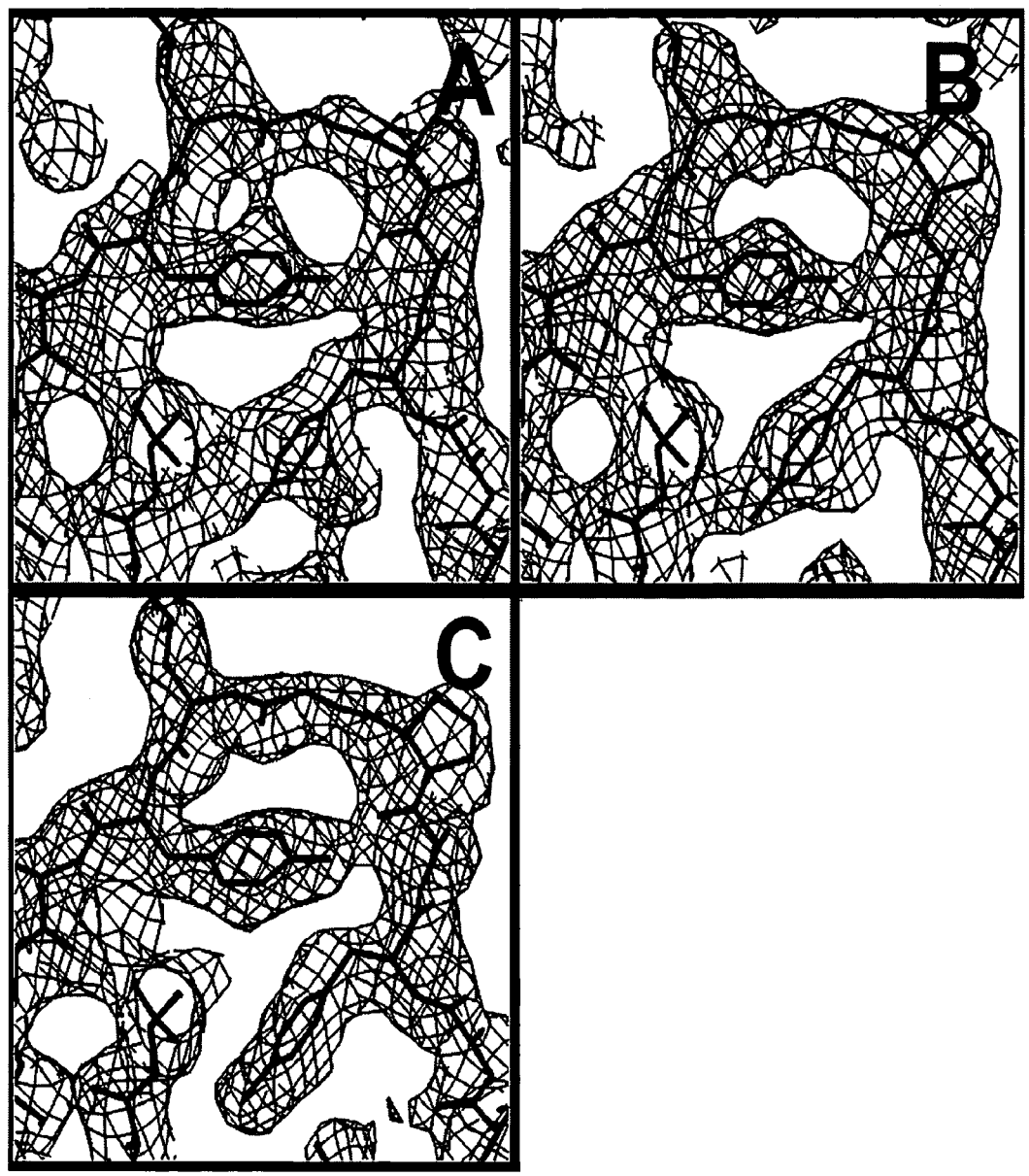
FIG. 15, Panels A–C illustrates the application of the process to modify an electron density map obtained by first applying the SOLVE process to an electron density map using experimental phases.

Referring to FIGS. 15, Panels A–C, the original SOLVE electron density map (Terwilliger et al., 1999) using experimental phases is shown in Panel A. This map has a correlation with the model gene 5 protein map of 0.56. The electron density map calculated from combined phases is shown in Panel B. This new electron density map has a correlation to the model map of 0.65. Finally, the combined phases and the experimental structure factor amplitudes were used in statistical density modification using the same parameters as those used to obtain the original RESOLVE phase probabilities. The resulting map is shown in Panel C; it is very similar to the original RESOLVE map shown in FIG. 13, Panel A, but it is slightly improved, with a correlation to the model gene 5 protein map of 0.82 (compared with 0.79 for the original RESOLVE map).

A key element of the process used here is to remove information about the density at each point x from the analysis of patterns of density around of x. We tested the importance of this step by repeating the entire process of generating templates and histograms, then applying them to the gene 5 protein MAD data, but without removing this information. In this case the recovered image had a higher correlation with the model map than in the test case described above (0.55 compared with 0.25), and the smoothed recovered image had a correlation of 0.59, compared with 0.42. On the other hand the correlation of errors between the recovered image and the starting RESOLVE map was also much higher (0.68 compared with 0.15), as was the correlation of errors between the smoothed recovered image and the starting RESOLVE map (0.85 compared with 0.23). Finally, the resulting combined phases were used as a starting point for density modification, but in this case no improvement in the final map was obtained (correlation coefficient with the model map of 0.79 in both cases), supporting the idea that this step is an important element in the process.

Iterative Local Pattern Identification and Density Modification

Table II summarizes the results of applying this process to experimental data from crystals of several different proteins. The greatest improvement was obtained for cases where the original RESOLVE map had a correlation with the model map of less than 0.7, with smaller improvements obtained when the RESOLVE map was better than this. In each of these cases, the templates and histograms were obtained from model maps calculated at a resolution of 2.6 Å. The use of templates at varying resolutions could increase the applicability of the method to a much wider resolution range.

TABLE II

| Structure | UTP-synthese (Gorden et al., 2001) | Armadillo repeat of □-catenin (Huber et al., 1997) | Gene 5 protein (Skinner et al., 1994) | Hypothetical (P. aerophilum ORF, NCBI accession number AAL64711; Fitz-Gibbon et al., 2002) | nusA (Shin, D. H., Nguyen, H. T., Jancarik, J., Yokota, H., Kim, R., Kim, S. H., unpublished; PDB entry 1L2F) | NDP Kinase (Pédelacq et al, 2002) |
|---|---|---|---|---|---|---|
| Resolution (Å) | 2.8 | 2.7 | 2.6 | 2.6 | 2.4 | 2.4 |
| Type of experiment | SAD | MAD | MAD | MAD | SAD | MAD |
| RESOLVE map correlation to model map (no local patterns) | 0.727 | 0.872 | 0.786 | 0.811 | 0.648 | 0.586 |
| RESOLVE map correlation to model map (with local patterns) | 0.760 | 0.874 | 0.815 | 0.821 | 0.847 | 0.649 |

REFERENCES

Incorporated Herein by Reference for all Purposes

Agarwal, R. C. et al., (1977) *Proc. Natl. Acad. Sci. USA* 74, 2835–2839.
Berman, H. M. et al., (2000) *Nucleic Acids Research* 28, 235–242.
Bernstein, B. E. et al. *J. Mol. Biol.* 279, 1137–1148.
Blaber M. et al., (1993) *Biochemistry* 32, 11363–11373.
Blundell and Johnson, (1996) *Protein Crystallography*, New York, Academic Press.
Bricogne, G., (1974) *Acta Cryst.* A30, 395–405.
Colovos, C., et al. (2000) *Acta Cryst.* D56, 1421–1429.
Cowtan, K., (1999) *Acta Cryst.* D55, 1555–1567.
Fitz-Gibbon, S. T., et al. (2002). *Proc. Natl. Acad. Sci. U.S.A.* 99, 984–989.
Funkhouser, T. et al., (2003) *ACM Transactions on Graphics*, 22, 83–105.
Goldstein, A. et al., (1998) *Acta Cryst.* D54, 1230–1244.
Gordon, E. J. et al., (2001). *J. Biol. Chem.* 276, 10999–11006.
Harrison, R. W. et al., (1988). *J. Appl. Cryst.* 21, 949–952.
Huber, A. H. et al., (1997). *Cell* 90, 871–882.
Jones, T. A. et al., (1991). *Acta Cryst.* A47, 110–119.
Nieh, Y. P. et al., (1999) *Acta Cryst.* D55, 1893–1900.
Kleywegt, G. J. et al., (1997) *Structure* 5, 1557–1569.
Kleywegt, G. J. et al., (1996). *Acta Cryst* D52, 826–828.
Lamzin, V. S. et al., (1993) *Acta Cryst* D49, 129–147.
Lunin, V. Y. et al., (1984) *Acta Cryst.* A40, 269–277.
Lunin, V. Y., (1988) *Acta Cryst.* A44, 144–150.
Morris, R. J. et al., (2002) *Acta Cryst.* D58, 968–975.
Peat T. S. et al., (1998). *Structure* 6, 1207–1214.
Pédelacq, J.-D. et al., (2002). *Nature Biotechnology*, 20, 927–932.
Perrakis, A. et al., (2001). *Acta Cryst.* D57, 1445–1450.
Perrakis, A. et al., (1997). *Acta Cryst.* D53, 448–455.
Perrakis, A. et al., (1999). *Nature Structural Biology* 6, 458–463.
Read, R. J., (1986). *Acta Cryst.* A42, 140–149.
Rossmann, M. G., (1972). *The molecular replacement method*. New York: Gordon & Breach.
Skinner, M. M. et al., (1994). *Proc. Natl. Acad. Sci. USA* 91, 2071–2075.
Terwilliger, T. C. et al., (1999). *Acta Cryst.*, D55, 501–505.
Terwilliger, T. C., (2000). *Acta Cryst.*, D55, 1863–1871.
Terwilliger, T. C. (2001). *Acta Cryst.*, D57, 1755–1762.
Terwilliger, T. C., (2003). *Acta Cryst.* D59, 38–44.
Terwilliger, T. C., (2002b). *Acta Cryst* D59, 45–49.
Wang, B.-C., (1985). *Methods Enzymol.* 115, 90–112.
Yarbrough, D. et al., (2001). *Proc. Natl. Acad. Sci. USA* 98, 462–467.
Zhang, K. Y. J. et al., (1997). *Methods Enzymol.* 277, 53–64.
Zhang, K. Y. J. et al., (1990). *Acta Cryst.*, A46, 41–46.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A computer implemented method for modifying an experimental electron density map comprising the steps of:
providing a set of selected known experimental and model electron density maps;
creating standard templates of electron density from the selected experimental and model electron density maps by clustering and averaging values of electron density in a spherical region about each point in a grid that defines each selected known experimental and model electron density maps;
creating histograms from the selected experimental and model electron density maps that relate the value of electron density at the center of each of the spherical regions to a correlation coefficient of a density surrounding each corresponding grid point in each one of the standard templates;

applying the standard templates and the histograms to grid points on the experimental electron density map to form new estimates of electron density at each grid paint in the experimental electron density map; and, outputting a modified electron density map.

2. The method of claim 1, wherein the steps of creating standard templates and creating histograms include the step of excluding electron density information from each grid point as clustering and averaging values are generated for that grid point and as histograms are generated for that grid point.

3. The method of claim 2, wherein the step of creating standard templates further includes the steps of:

generating three separate sets of templates corresponding to grid points that have either low, medium, or high electron density;

selecting a subset of templates from the three sets of templates that have a low mutual correlation; and selecting a final set of templates from the subset of templates that are selected to maximize the predictive power of the final set of templates.

4. The method of claim 2, where the step of creating histograms includes the steps of:

comparing the electron density value at each grid point in each of the templates with the electron density value at corresponding grid points in a set of high quality electron density maps and determine a correlation coefficient at each grid point;

identifying two templates that have the highest and next-highest correlation coefficients; and tabulating the value of the electron densities in the two templates and normalize to yield an estimate of the probability distribution of an electron density at each grid point.

5. The method of claim 1, wherein the step of creating standard templates further includes the steps of:

generating three separate sets of templates corresponding to grid points that have either low, medium, or high electron density;

selecting a subset of templates from the three sets of templates that have a low mutual correlation; and selecting a final set of templates from the subset of templates that are selected to maximize the predictive power of the final set of templates.

6. The method of claim 1, where the step of creating histograms includes the steps of:

comparing the electron density value at each grid point in each of the templates with the electron density value at corresponding grid points in a set of high quality electron density maps and determine a correlation coefficient at each grid point;

identifying two templates that have the highest and next-highest correlation coefficients; and tabulating the value of the electron densities in the two templates and normalize to yield an estimate of the probability distribution of an electron density at each grid point.

7. The method of claim 1, further including the step of combining the modified electron density map with the experimental electron density map to provide a new electron density map having improved quality.

* * * * *